United States Patent [19]
Allard et al.

[11] Patent Number: 5,275,600
[45] Date of Patent: Jan. 4, 1994

[54] TELESCOPING ROD TO ROD COUPLER FOR A SPINAL SYSTEM

[75] Inventors: Randell N. Allard, Plymouth; Joseph R. Korotko, Fort Wayne, both of Ind.

[73] Assignee: Zimmer, Inc., Warsaw, Ind.

[21] Appl. No.: 956,199

[22] Filed: Oct. 5, 1992

[51] Int. Cl.⁵ .............................................. A61B 17/56
[52] U.S. Cl. ......................................... 606/61; 606/72
[58] Field of Search ........................................ 606/53-

[56] References Cited

U.S. PATENT DOCUMENTS

| | | | |
|---|---|---|---|
| 4,308,863 | 1/1982 | Fischer | 606/57 |
| 4,404,967 | 9/1983 | Bacal | 606/61 |
| 4,445,513 | 5/1984 | Ulrich | 606/61 |
| 4,611,582 | 9/1986 | Duff | 606/61 |
| 4,624,249 | 11/1986 | Alvarez Cambras | 606/57 |
| 4,931,055 | 6/1990 | Bumpus | 606/61 |
| 4,938,768 | 7/1990 | Wu | 606/60 |
| 4,957,495 | 9/1990 | Kluger | 606/61 |
| 5,019,077 | 5/1991 | De Bastiani | 606/57 |

FOREIGN PATENT DOCUMENTS 0452792 10/1991 European Pat. Off. .............. 606/59

Primary Examiner—Michael A. Brown
Attorney, Agent, or Firm—Todd A. Dawson

[57] ABSTRACT

The telescoping rod to rod coupler of this invention substantially eliminates the chances of the two rod sections disconnecting from one another by providing a relief in the male section to define a hook shaped end. The hook shaped end in association with a clamping screw carried by the female section requires the rod sections to axial rotate 180 degrees in a screw-like manner during assembly and disassembly. The clamping screw constitutes an abutment or stop for engagement with the hook shaped end to provide a positive stop to prevent the sections from accidentally sliding past their extremes and out of engagement with one another during the surgery. Further, the reliefs provided within the male telescoping section, permit the two rod sections to be firmly affixed to one another with one section axially rotated slightly relative to the other rod section.

2 Claims, 5 Drawing Sheets

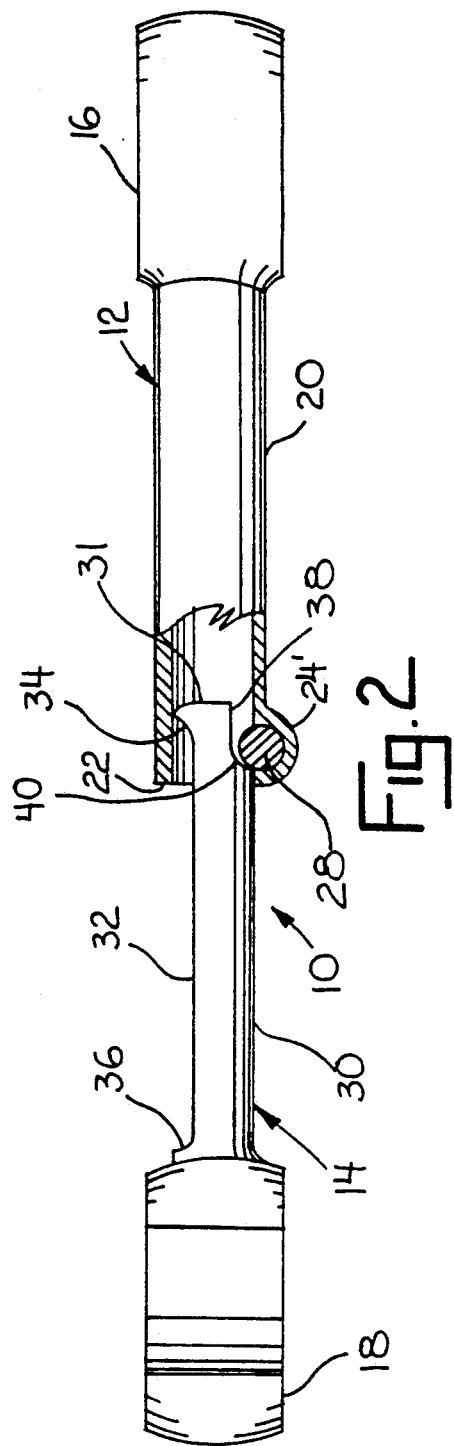
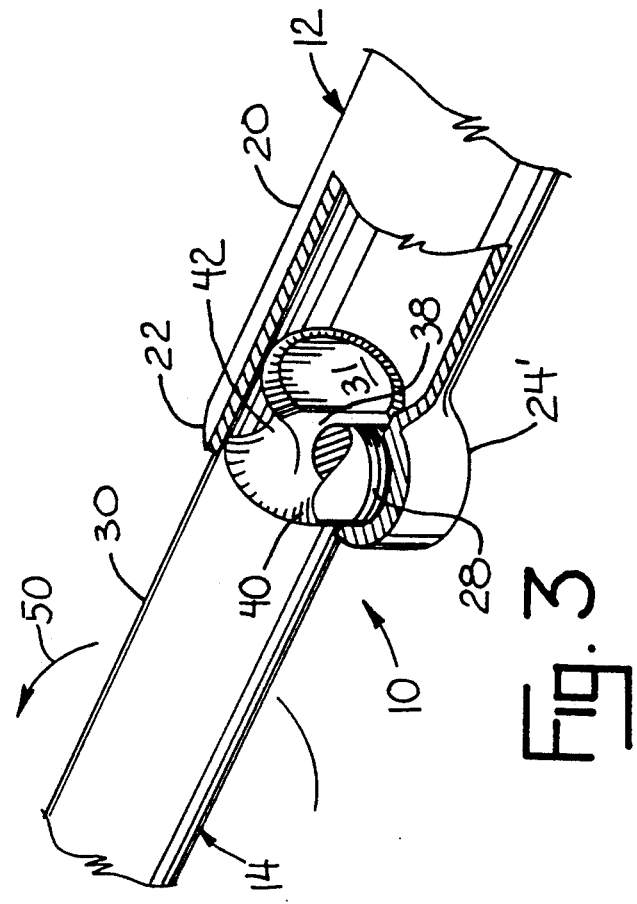

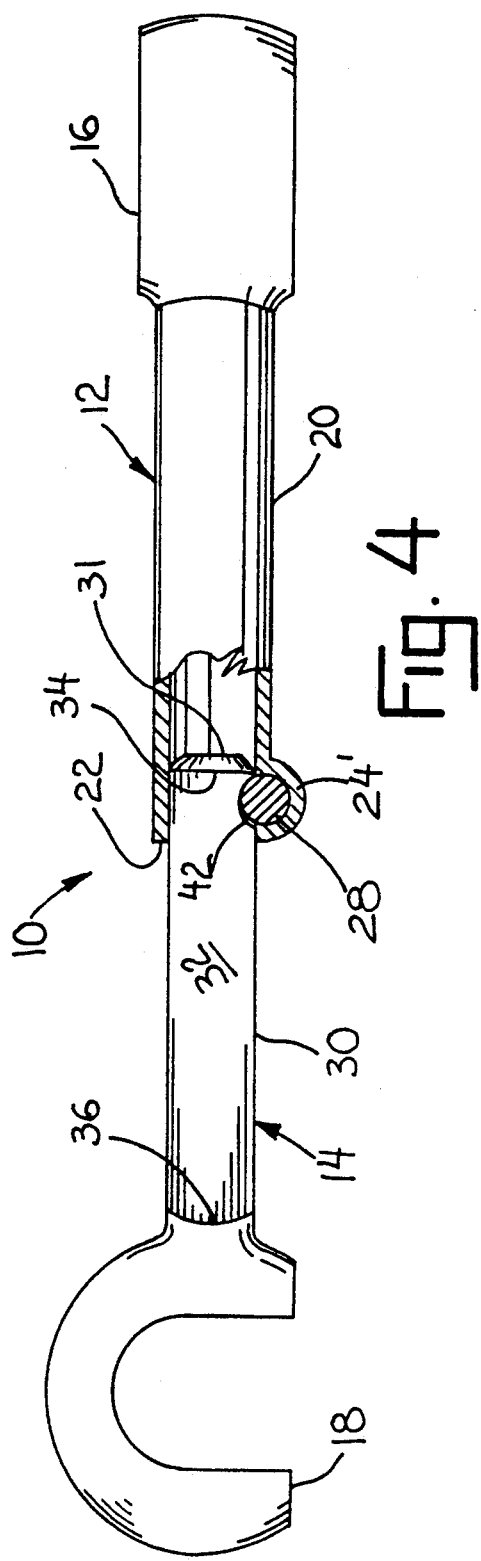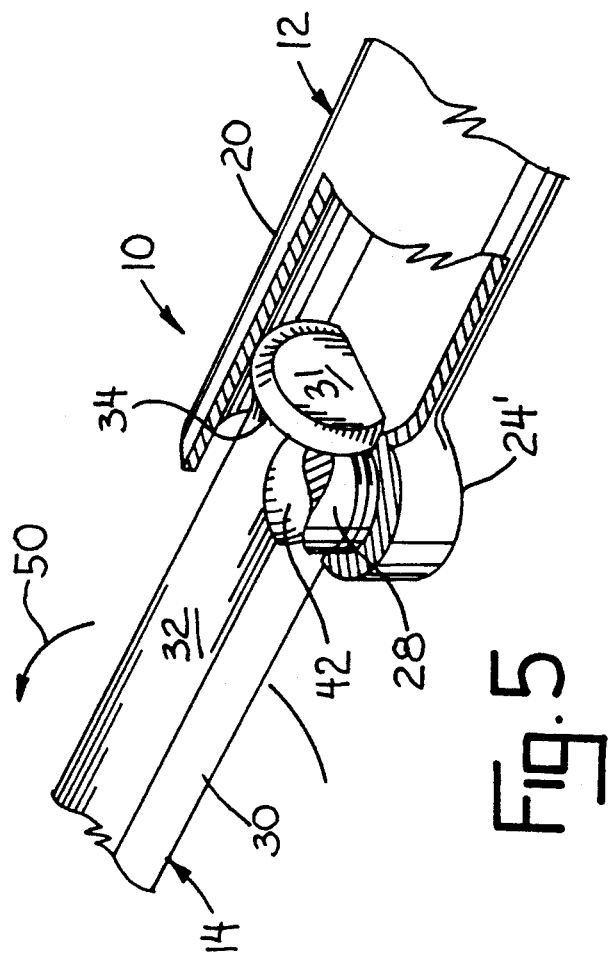

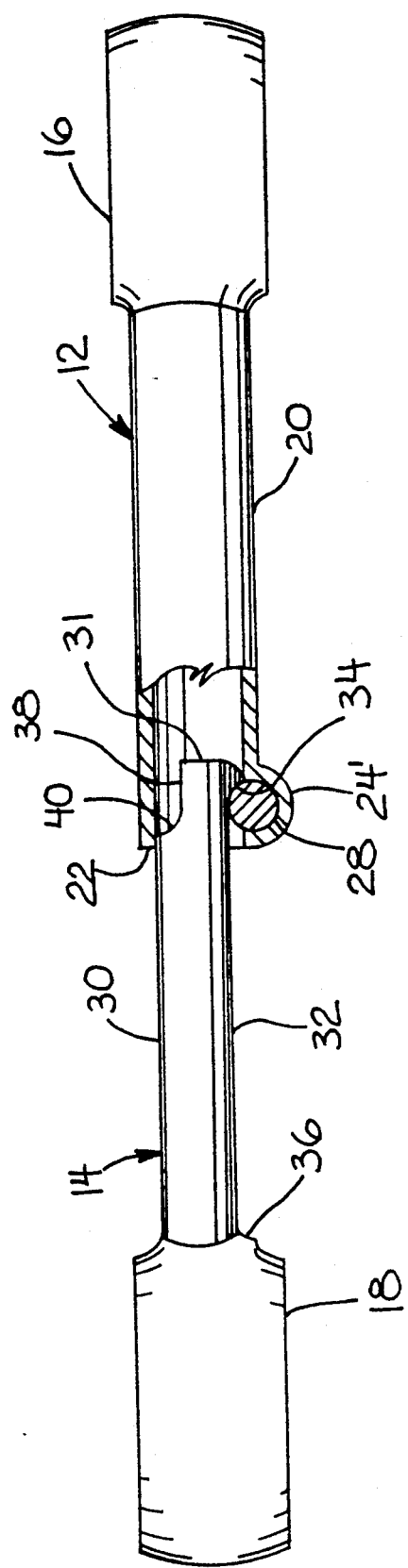
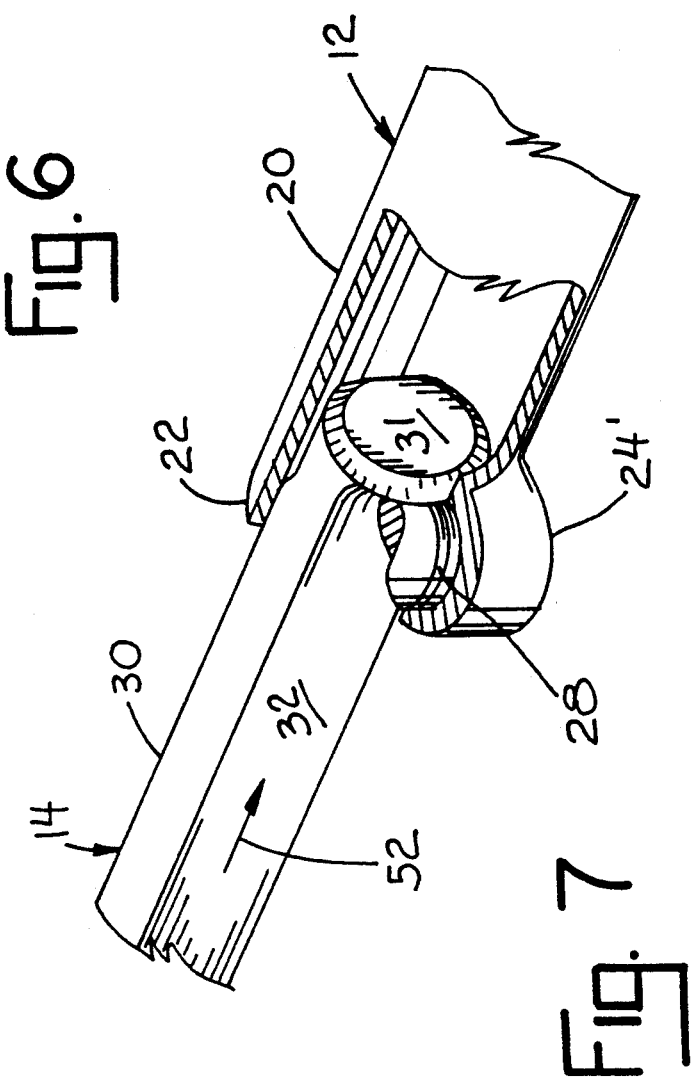
Fig. 6
Fig. 7

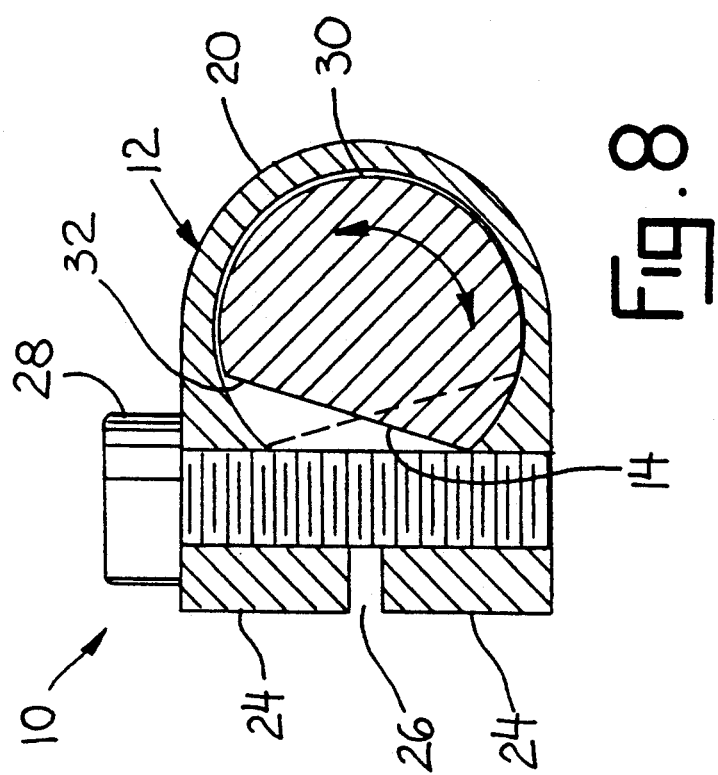

TELESCOPING ROD TO ROD COUPLER FOR A SPINAL SYSTEM

BACKGROUND OF THE INVENTION

This invention relates to telescopic rod to rod couplers for use in a spinal implant system to fix a pair of generally parallel spinal rods in a spaced relationship. The telescopic rod sections are assembled together using a 180 degree twisting motion which minimizes the risk of the rod sections accidentally disconnecting during the implant procedure.

In the field of spinal surgery it is common for a surgeon to attach a pair of generally parallel rods to the spinal column to assist in the correction of spinal deformities. A variety of couplers have been disclosed and patented for coupling the spinal rods to the individual vertebra so that tension or compressive forces may be applied to the vertebra for correcting the malady. It may be necessary, during the spinal implant surgery, for the surgeon to couple the spinal rods together using a rod to rod coupler to provide additional stability for the spinal system. A variety of spinal rod to rod couplers are known to achieve the interconnection of the two rods. Generally, such couplers include some type of slide or telescopic device to accommodate the variety of spacings between the rods encountered during surgery. Generally, a locking member of some configuration is provided to securely lock the two telescoping sections together and prevent further telescopic movement.

Heretofore, prior art rod to rod couplers are formed such that prior to the locking member being engaged, the telescoping sections may be easily slid past their extremes and out of engagement with one another. While this is a convenient method of connecting and disconnecting the coupler sections, it can be inconvenient during surgery if the sections accidentally disengage.

SUMMARY OF THE INVENTION

The telescoping rod to rod coupler of this invention substantially eliminates the chances of the two rod sections disconnecting from one another by providing a relief in the male section to define a hook shaped end. The hook shaped end in association with a clamping screw carried by the female section requires the rod sections to axial rotate 180 degrees in a screw-like manner during assembly and disassembly. The clamping screw constitutes an abutment or stop for engagement with the hook shaped end to provide a positive stop to prevent the sections from accidentally sliding past their extremes and out of engagement with one another during the surgery.

Further, the relief provided within the male telescoping section permits the two rod sections to be firmly affixed to one another with one section axially rotated slightly relative to the other rod section.

Accordingly, it is an object of the invention to provide a novel rod to rod coupler for a spinal system, wherein the telescoping rod sections axially rotate 180 degrees relative to one another to connect or disconnect the rod sections.

Another object of the invention is to provide a rod to rod coupler for a spinal system wherein the telescoping rod sections may be connected to one another slightly axially rotated relative to one another.

Another object of the invention is to provide for a novel rod to rod coupler for a spinal system having a positive stop mechanism to prevent the telescoping sections from sliding past their extremes and disengagement from one another during their use.

Still other objects of the invention will become apparent upon a reading of the following description taken with the accompanying drawings.

BRIEF DESCRIPTION OF THE DRAWINGS

FIGS. 2, 4, and 6 are plan views of the rod to rod coupler of the invention with portions cut away for illustrative purposes. The male portion of the telescoping rod section is illustrated in FIGS. 2, 4, and 6 as progressively rotating from the initial contact position of FIG. 2 to the fully rotated position of FIG. 6. FIG. 4 is a midway point of rotation of the male telescoping rod.

FIG. 3 is a partial perspective view of FIG. 2 with portions cut away for illustrative purposes.

FIG. 5 is a partial perspective view of FIG. 4 with portions cut away for illustrative purposes.

FIG. 7 is a partial perspective view of FIG. 6 with portions cut away for illustrative purposes.

FIG. 8 is a sectional view of the telescoping rod.

DETAILED DESCRIPTION OF THE INVENTION

Figure 1:
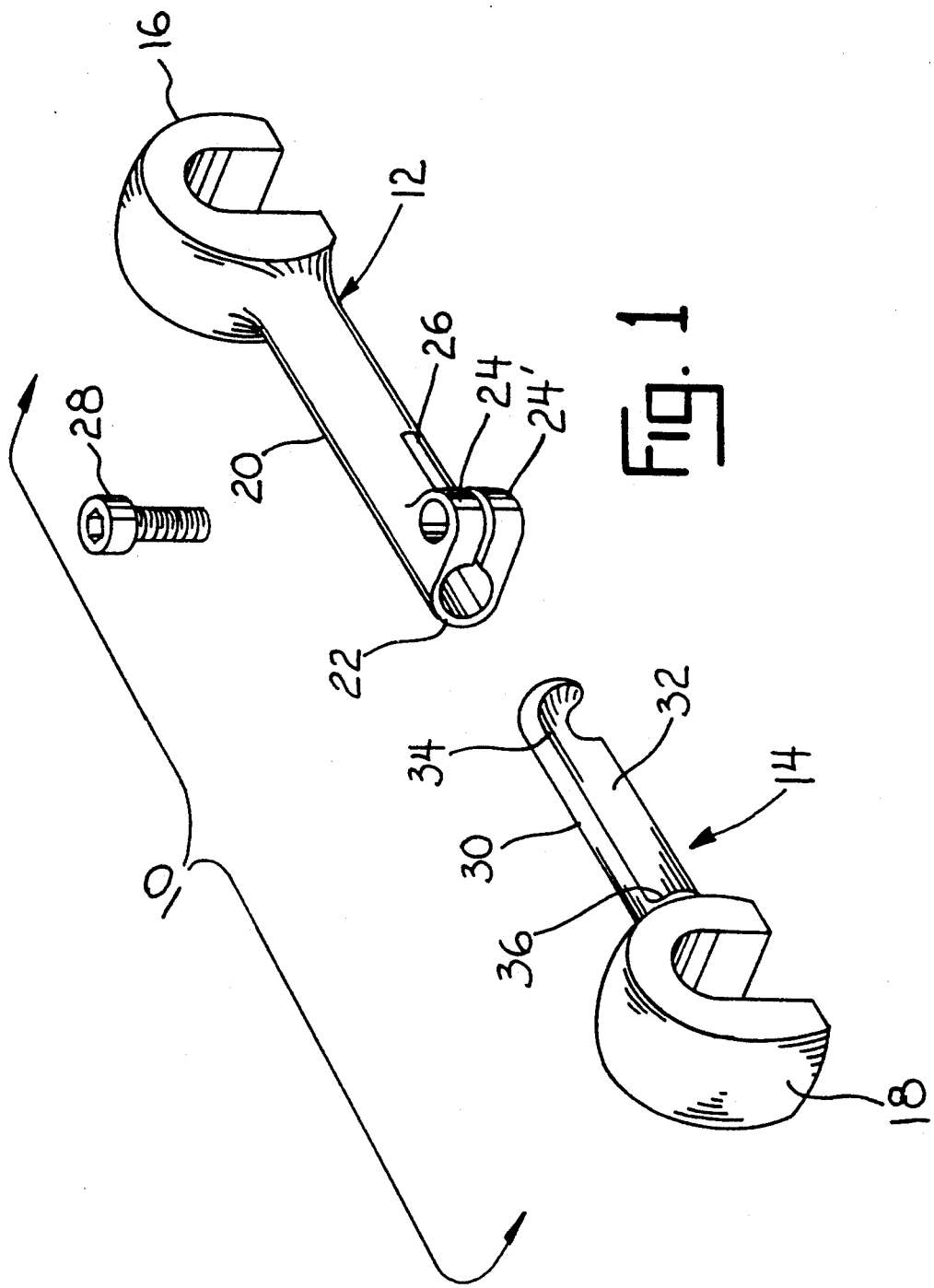
FIG. 1 is an exploded perspective view of the rod to rod coupler of the invention.

The preferred embodiment herein described is not intended to be exhaustive nor to limit the invention to the precise form disclosed. Rather, it is chosen and described to best explain the invention so that others skilled in the art might utilize its teachings.

Referring now to the drawings, rod to rod coupler 10 includes a female telescoping rod section 12 and a male telescoping rod section 14. Rod section 12 includes at one end a C-shaped coupler body 16 for engagement with a spinal rod (not shown). Likewise, rod section 14 includes at one end a C-shaped coupler body 18 for engagement with a spinal rod (not shown). The specifics on the design and use of the coupler bodies and the particulars on their clamping attachment to a spinal rod are not discussed here. Such devices are known in the industry and have no bearing on the novelty of the particular invention of a rod to rod coupler as described herein.

Female rod section 12 includes a generally tubular body 20 integrally extending from coupler body 16 and defining a generally cylindrical interior space opening at end 22. A pair of flanges 24, 24' extend integrally outwardly from body 20 adjacent end 22. A slot 26 is formed in body 20 between the flanges and extends from end 22. Each flange includes a bore therethrough for accommodating locking screw 28 with the bore in flange 24' being threaded. As illustrated in the figures, locking screw 28 is in communication with the interior of body 20 and forms an interference therein.

Male rod section 14 includes a rigid shaft 30 integrally extending from coupler body 18. A recess is formed in shaft 30 defining a flattened area 32 terminating in arcuate shoulders 34, 36. A recess 38 is formed in shaft 30 from end 31 and terminates in arcuate shoulder 40. Recess 38 is formed on an opposite side of shaft 30 as flattened area 32. An arcuate notch 42 is formed about shaft 30 adjacent end 31 extending from flattened area 32, adjacent shoulder 34, to recess 38, adjacent shoulder 40. The combination of flattened area 32, recess 38 and arcuate notch 42 form a generally hook shaped projection 44 on end 31 of the shaft having a generally D-shaped face (see FIG. 3).

To assemble rod sections 12 and 14 into telescopic engagement with one another, the male rod section 14 is rotated 180 degrees relative to the female rod section 14 such that the C-shaped coupler bodies open in opposite directions as illustrated in FIG. 2. So positioned, end 31 of shaft 30 may be inserted into end 22 of body 20. As illustrated in FIGS. 2 and 3, recess 30 accommodates a portion of the locking screw 28, such that the portion of the screw forming an interference within body 20 contacts arcuate shoulder 40 to halt further progression of the shaft into the body at this point. In the position of FIGS. 2 and 3, the portion of the screw forming the interference within body 20 is in alignment with arcuate notch 42 of shaft 30.

Male rod section 14 is then rotated relative to female rod section 12 in the direction of arrow 50 such that arcuate notch 42 passes over the screw portion forming an interference. FIGS. 4 and 5 illustrate the orientation of arcuate notch 42 and screw 28 during rotation of rod section 14 relative to rod section 12. Since the screw portion forming an interference is accommodated within the arcuate notch 42, the rod sections 12 and 14 are unable to slide longitudinally relative to one another at this point of the assembly or disassembly of the rod sections.

Continued rotation of the male rod section 14 relative to the female rod section 12 in the direction of arrow 50 brings arcuate shoulder 34 of flat 32 into contact with screw 28 to stop further rotation of the male section in the direction of arrow 50. As illustrated in FIGS. 6 and 7, with the screw in abutting contact with shoulder 34, the screw portion forming an abutment is aligned with flat 32 of shaft 30. In this position, male shaft 14 may be slid in the direction of arrow 52 for telescopic adjustment of the distances between C-shaped bodies 16 and 18. It should be noted that in the fully rotated position of FIGS. 6 and 7, the openings of the C-shaped bodies face the same direction (see FIG. 6).

When the telescopic rods are spaced sufficiently for the surgeon and the coupler bodies 16 and 18 are clamped to the spinal rods (not shown) by a clamping device (also not shown), the locking screw 28 is tightened to compress end 22 of rod section 12 about the male rod section 14. When screw 28 is tightened a sufficient amount, the rod sections are rigidly fixed against longitudinal or axial movement relative to one another.

In use, in the rod to rod coupler 10 may be connected to spinal rods which are not fully co-planar. FIG. 8 illustrates a cross section of the coupler 10 taken near locking screw 28 when the coupler 10 is connected to spinal rods (not shown) which are not fully co-planar. FIG. 8 is included to illustrate the point that the rod sections 12 and 14 may be clamped together by locking screw 28 with rod section 14 not fully rotated into the position of FIGS. 6 and 7 yet screw 28 is accommodated by flat 32.

It should be understood that the invention is not to be limited to the details above, but may be modified within the scope of the pending claims.

We claim:

1. A rod to rod coupler for a spinal system adapted for connection between a pair of spaced spinal rods to maintain the spinal rods a fixed distance relative to one another, said rod to rod coupler comprising a male section having a solid rigid shaft having at one end a coupler body adapted for engagement with one of said pair of spaced spinal rod and another end, a female section having a generally tubular body being open at one end and at another end having a coupler body adapted for engagement with one of said pair of spaced spinal rods, said male section including a first longitudinal relief extending from said another end into said shaft and a second relief extending substantially all along said shaft, said first and second relief being on opposite sides of said shaft, said male section further including an arcuate notch formed adjacent said another end and in communication with said first relief and said second relief, said female section including an abutment extending partially into said tubular body adjacent said one end, said first relief and said arcuate notch forming a thread means for engagement with said abutment such that connection of said male section and said female section requires said male section to axially rotate relative to said female section, said abutment being accommodated first by said first relief and then by said arcuate notch and finally by said second relief as said male section is rotated relative to said female section, wherein with said abutment being accommodated by said second relief said male section and said female section are telescopically connected with said shaft sliding within said tubular body.

2. The rod to rod coupler of claim 1 further including a locking screw carried by said female section for clamping said female section to said male section, wherein a portion of said locking screw constitutes said abutment.

* * * * *